United States Patent [19]

Hosoda et al.

[11] Patent Number: 5,366,861
[45] Date of Patent: Nov. 22, 1994

[54] IMMUNOASSAY AND REAGENT KIT USED THEREFOR

[75] Inventors: Kenji Hosoda, Kawagoe; Takaharu Kubota; Hitomi Honda, both of Hino; Hideaki Suzuki, Koganei, all of Japan

[73] Assignee: Teijin Limited, Osaka, Japan

[21] Appl. No.: 26,110

[22] Filed: Mar. 1, 1993

Related U.S. Application Data

[63] Continuation of Ser. No. 815,868, Jan. 3, 1992, abandoned, which is a continuation of Ser. No. 362,415, filed as PCT/JP88/00802, Aug. 12, 1988, abandoned.

[30] Foreign Application Priority Data

Aug. 12, 1987 [JP] Japan .................................. 62-200043
Nov. 10, 1987 [JP] Japan .................................. 62-281975

[51] Int. Cl.$^5$ .................. C12Q 1/00; C12Q 1/48; G01N 33/536
[52] U.S. Cl. .................................. 435/7.1; 435/7.92; 435/7.93; 435/7.94; 435/7.95; 435/15; 435/975; 436/536
[58] Field of Search ............... 436/536; 435/7.1, 7.92, 435/7.93, 7.94, 7.95, 15, 975

[56] References Cited

U.S. PATENT DOCUMENTS 5,156,950 10/1992 Akino et al. ...................... 435/7.51

FOREIGN PATENT DOCUMENTS 0224590 6/1987 European Pat. Off. ... G01N 33/577
0260903 3/1988 European Pat. Off. ..... G01N 33/53

OTHER PUBLICATIONS

Hussain et al., *J. Virol. Meth.* 19 (1988) 207–214.
Kuroki et al. *Ped. Res.* 19 (1985) 1017–1020.
Baldo et al. *J. Bioch. Bioph. Meth.* 12 (1986) 271–279.
Hybridoma, vol. 9, No. 2, 1990, "Determination of Antigenic Epitopes Recognized by Four Monoclonal Antibodies to Glutathione S–Transferase".
Supplementary European Search Report.
Choi et al, "Isolation and Characterization of a 35000 Molecular Weight Subunit Fetal Cartilage Matrix Protein," The Journal of Biological Chemistry, vol. 258, No. 1, pp. 655–661, Jan. 1983.
Journal of Clinical Microbiology, vol. 25, No. 3 (Mar., 1987) pp. 509–515.

*Primary Examiner*—Margaret Parr
*Assistant Examiner*—Bradley L. Sisson
*Attorney, Agent, or Firm*—Sughrue, Mion, Zinn, Macpeak & Seas

[57] ABSTRACT

An immunoassay method performed in solution wherein a protein having an average molecular weight of 16,000 to 50,000 and an isoelectric point of 1.0 to 5.0 or a mixture containing the same is permitted to exist as the antigen-antibody reaction controller in the immunoreaction solution, and the final concentration of the antigen-antibody controller in the immunoreaction solution is controlled to 0.02 to 0.9% by weight, and a reagent kit to be used for an immunoassay containing the above antigen-antibody reaction controller at a final concentration of 0.02 to 0.9% by weight in the immunoreaction solution, as a part of the constituents thereof.

6 Claims, 14 Drawing Sheets

IMMUNOASSAY AND REAGENT KIT USED THEREFOR

This is a continuation of application Ser. No. 07/815,868 filed Jan. 3, 1992, now abandoned, which is a continuation of application Ser. No. 07/362,415 filed as PCT/JP88/00802, Aug. 12, 1988, now abandoned.

TECHNICAL FIELD

The present invention relates to an immunoassay and a reagent kit used therefor, whereby an amount of a substance is assayed immunologically by utilizing an antigen-antibody reaction in a solution, wherein the nonspecific reactions are reduced without lowering the specific reaction.

BACKGROUND ART

Immunoassay methods using antibodies are used widely due to the high levels of specificity and sensitivity thereof, and the development thereof is expected to increase due to the discovery of monoclonal antibodies in 1975.

Previously radioactive substances, such as ($I^{125}$) were used as the means of detection in an immunoassay, but in recent years enzymes and fluorescent substances and the like are used. As a result, expertise in the handling of radioactive substances is no longer required and that is one reason for the accelerated spread of the use of immunoassays.

To achieve a high level of sensitivity in immunoassay, the specific reaction derived from the antigen-antibody reaction must be strong and the other nonspecific reactions must be very weak.

The suppression of the nonspecific reactions is technically important in the perfection of a high sensitivity immunoassay, and therefore, various attempts have been made to achieve same. The most widely practiced means is to include an additive for the suppression of nonspecific reactions into the immunoreaction system. Those means may be classified broadly into two categories: the use of a surfactant, which is nonproteinaceous substance, and the use of a body fluid or a protein solution. As an example of the first method, in Japanese Unexamined Patent Publication (Kokai) No. 57-182169, a soluble polyanion is used as the reaction medium for carrying out the immunoreaction, or in Japanese Unexamined Patent Publication (Kokai) No. 58-187862, a nonspecific adsorption elimination method is disclosed. As examples of the second method, in Japanese Unexamined Patent Publication (Kokai) No. 59-25184 0.1% or more of a hydrophobic protein in the presence of a salt, is used or a reduction of nonspecific adsorption is obtained by the use of mouse ascites, as in Japanese Unexamined Patent Publication (Kokai) No. 61-65162.

The prior art methods as described above have drawbacks and are not fully satisfactory as nonspecific adsorption elimination methods under the present circumstances.

More specifically, the first method frequently will interfere with the specific reaction resulting in an assay system having low sensitivity. Although the use of a hydrophobic protein has been mentioned as a second method, according to investigations made by the instant inventors, hydrophobicity had substantially no nonspecific adsorption elimination effect.

Further, when mouse ascites are used as in the second method, the problem arises in the reproducibility of the components of the ascites, and the specific reaction may be reduced by these components, contrary to the object of immunoassay per se.

Nevertheless, there are great expectations for the achievement of high sensitivity by an immunoreaction on a membrane, such as nitrocellulose or the like, through a concentration of the antigen on the membrane rather than in the above-mentioned solution; and this technique has become widely used. report in *J. Biochem. Biophys. Methods* 12, 271 to 279 (1986), the observation of a striking reduction in the nonspecific reactions by blocking a membrane using a 10% suspension of skim milk.

As the solid-phase reaction blocking agent, Ahmad et al. used skim milk. In the *J. Clin. Microbiol.* 23, 3, 563 to 567 (1986), Ahmad et al. measured the anti-pseudorabies virus antibodies in the serum of patients by blocking a nitrocellulose membrane carrying immobilized pseudorabies virus using a 5% skim milk solution.

However, if a 5% to 10% skim milk suspension is used as the blocking agent, as stated in the report by Baldo et al, there is a large decline in the specific reaction and thus a loss of one of the two essential conditions for high sensitivity of an immunoassay (a high specific reaction derived from the antigen-antibody reaction) and a resulting inability to achieve a highly sensitive assay.

The reason for the inhibition of the specific reaction is that skim milk is insoluble in water at that concentration and essentially is a suspension. When observed under a microscope, large insoluble particles of the skim milk cover the antigen preventing the antibodies from approaching the same, and as a result, considerably inhibiting the antigen-antibody reaction.

The use of skim milk as a blocking agent in the prior art is used commonly in the above-mentioned solid phase immunoreaction but not often in the case of an immunoreaction in the solution phase.

In the past, there has only been one report on the use of skim milk as an additive in an immunoreaction in the solution phase; that report was made by Kuroki et al. in *Pedialr. Res.* 19, 1017 (1985), a 2% skim milk suspension was used for an assay of lung-surfactant apoprotein in amniotic fluid. Two major problems arose in the use of skim milk in this method; first, that the suspension of skim milk was used so the specific immunoreaction was suppressed for the reason mentioned above, and second, that in the 2% skim milk suspension, precipitation occurs after two or three weeks storage in a refrigerator and it is impossible to redissolve the precipitate, thus resulting in a loss of the ability for inhibiting nonspecific reactions. In other words, the suspension must be used immediately after preparation or the function for inhibiting nonspecific reactions is lost and thus it is most unsatisfactory as a reagent.

DISCLOSURE OF THE INVENTION

Therefore, an object of the present invention is to solve the problems of the prior art as described above and provide an immunoassay and a reagent kit to be used therefor capable of maximizing an immunoassay reaction by suppressing nonspecific reactions without substantially lowering the specific reaction assay.

Other objects and advantages of the present invention will become apparent from the following description.

According to the present invention, there is provided an immunoassay which is performed in solution, wherein a protein having an average molecular weight of 16,000 to 50,000 and an isoelectric point of 1.0 to 5.0 or a mixture containing the same is permitted to exist as the antigen-antibody reaction controller in the immunoreaction solution, and the final concentration of the antigen-antibody controller in the immunoreaction solution is 0.02 to 0.9% by weight.

According to the present invention, there is further provided a reagent kit to be used for an immunoassay, containing a protein having an average molecular weight of 16,000 to 50,000 and an isoelectric point of 1.0 to 5.0 or a mixture containing the same as the antigen-antibody reaction controller to a final concentration of 0.02 to 0.9% by weight in the antigen-antibody reaction solution, as a part of the constituents thereof.

In the present invention, the "average molecular weight" of the protein means the molecular weight measured by the osmotic pressure method. Specifically, the average molecular weight of a protein is measured by utilizing the fact that when a polymer solution and a pure solvent are placed in contact with a semipermeable membrane which permeates freely the solvent molecules but not the solute polymer as the boundary therebetween, the osmotic pressure difference between both liquids is a parameter of the molecular weight of the polymer; in the present invention, it is a value measured at 4° C. by use of a 6.66M urea solution. The "isoelectric point" refers to the value measured by the chromatofocusing method, which separates proteins according to their molecular weights, specifically the value measured by using of a column (0.5 cm$\phi$ × 45 cm) filled with PBE gel (produced by Pharmacia Fine Chemicals) with an eluant of 0.025M imidazole hydrochloric acid solution (pH 7.4).

DETAILED DESCRIPTION OF THE PREFERRED EMBODIMENTS

Figure 1:
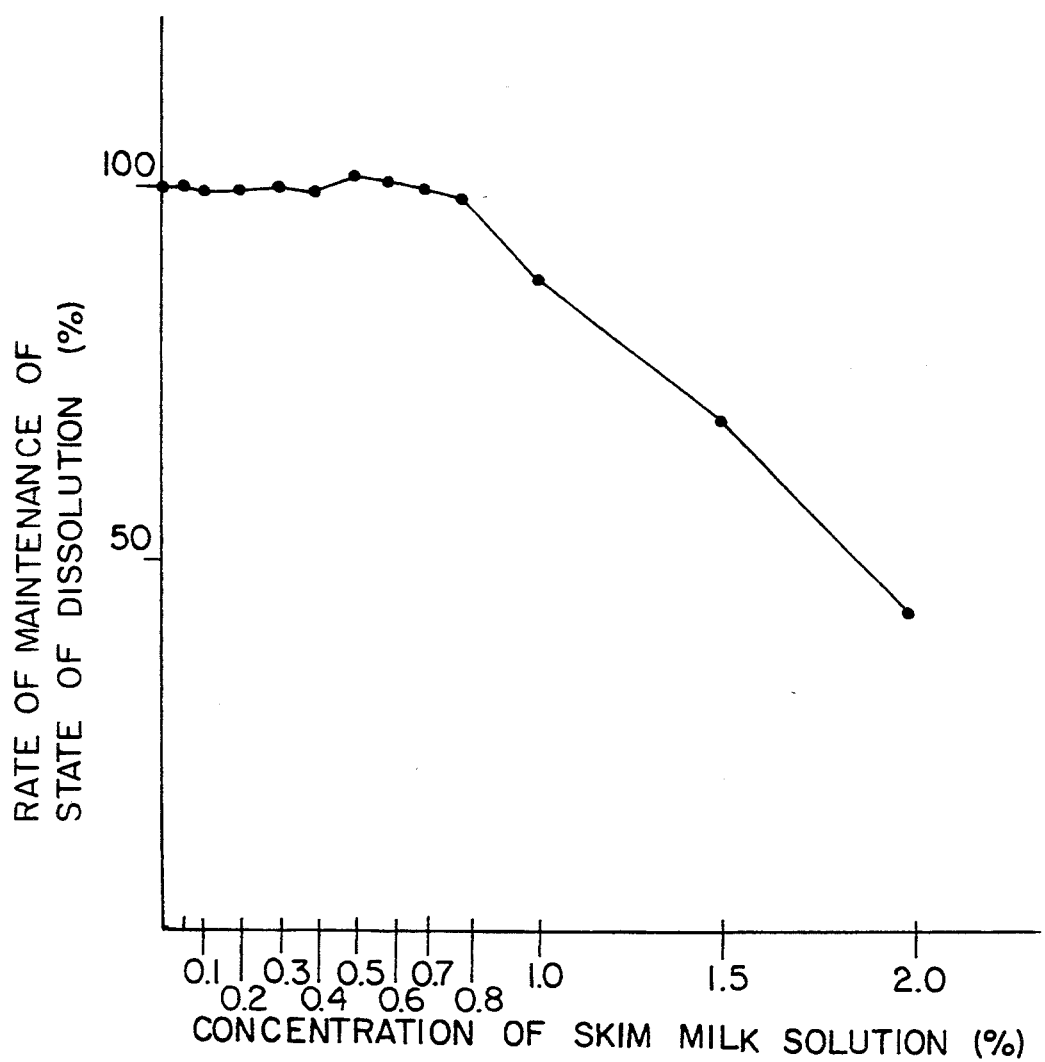
FIG. 1 shows the rate of maintenance of a dissolved state during storage of aqueous skim milk solutions of various concentration.

In the present invention, when performing an immunoassay utilizing an antigen-antibody reaction in a solution, a protein having a molecular weight of 16,000 to 50,000, preferably 20,000 to 46,000 and an isoelectric point of 1.0 to 5.0, preferably 1.2 to 4.8, is used as the antigen-antibody reaction controller in the immunoreaction solution.

As the protein in the present invention, casein, pepsin, ovoglycoprotein and orosomucoid may be included. When a protein with a molecular weight less than 16,000 is used, the nonspecific adsorption tends to become increased and but if it exceeds 50,000, the immunological nonspecific reactions are reduced insufficiently and the specific immunoreaction is lowered. Therefore, the molecular weight of the protein to be used in the present invention is 16,000 to 50,000, preferably 20,000 to 46,000.

On the other hand, for the isoelectric point, when a protein with an isoelectric point in excess of 5.0 is added, the nonspecific adsorption will be increased, and with an isoelectric point less than 1.0, the specific reaction will be suppressed. Therefore, the isoelectric point of the protein to be used in the present invention is 1.0 to 5.0, preferably 1.2 to 4.8.

According to the present invention, a mixture containing the protein as described above can be used as the antigen-antibody reaction controller. The mixture contains, for example, as the main ingredients, 10 to 60% by weight, preferably 20 to 50% by weight of the above protein, 30 to 80% by weight, preferably 40 to 60% by weight, of sugar (e.g. lactose), otherwise fats (e.g. 0.5 to 2% by weight) ash (e.g. 5 to 12% by weight), and water (e.g. 2 to 8% by weight). A typical example of such a mixture is skim milk. Skim milk contains casein as protein, but compared with the case when casein is used alone, skim milk has the specific features of good dispersibility in an immunoreaction solution, high NSB (Non-specific binding) per unit weight of protein and good storability at a temperature of 4° C. (non-formation of precipitate). As the skim milk for the present invention, defatted milk from any source may be used, most typically a commercially available skim milk manufactured by Difco.

The protein solution (or skim milk solution) in the present invention may be prepared as follows. That is, a protein with an adequate concentration or a mixture thereof (e.g., skim milk) is added to a phosphate buffered physiological saline, followed by stirring for one hour. The mixture is sonicated and may be passed through a 0.45 μM filter. When immunoassays are practiced by using protein solutions (or skim milk solutions) with various concentrations, nonspecific reactions were increased remarkably when a protein solution (or skim milk solution) of less than 0.02% by weight was used, even though the antigen amount was 0, and therefore the lower limit of the protein concentration is 0.02% by weight. On the other hand, at a concentration of more than 0.9% by weight, the specific immunoreaction was lowered, and the storage stability in a refrigerator also was lowered, and thus the upper limit of the protein concentration is 0.9% by weight. In view of the above, the protein concentration which satisfies the stability of the reagent and effectively reduces nonspecific reactions is preferably from 0.02 to 0.9% by weight, more preferably 0.05 to 0.7% by weight.

The reagent kit to be used for immunoassay according to the present invention is a known reagent kit, for example, a reagent kit to be used for immunoassay according to the sandwich method using two antibodies, consisting of (a) an enzyme-labelled antibody, (b) antibody-fixed beads, (c) an assay buffer, (d) a substrate solution, (e) a color forming agent, (f) a color formation stopping solution, (g) a standard, (h) a washing solution, and preferably, containing a solution of the above protein in any thereof. Among the above, preferably (a) an enzyme-labelled antibody or (c) an assay buffer, particularly (c) an assay buffer, is incorporated. The protein solution may be maintained in the lyophilized state, and reconstituted by dissolving in water before use, to a desired concentration.

According to the present invention, the addition of a protein which satisfies the conditions of the present invention or a mixture containing the same (typically skim milk) to the immunoassay system, confirms that nonspecific reactions can be lowered sufficiently without substantially lowering the specific reaction, whereby an immunoassay having a high sensitivity is obtained.

A solution of skim milk capable of exhibiting the blocking action of the prior art was susceptible to agglomeration of skim milk when left to stand for even a short period of time, whereby precipitates appeared which could not be dissolved. In that state, the blocking action of skim milk also disappeared. Nevertheless, when skim milk of the present invention is used as the antigen-antibody reaction controller, namely a skim milk solution of 0.02% by weight to 0.9% by weight is used in the present invention, an agglomerated mass will not be generated even when stored in a refrigerator as an aqueous solution for one year, and therefore, it can be utilized for an immunoassay and has a satisfactory storage stability as an assaying reagent.

Further, when an immunoreaction is carried out by using the skim milk solution thus prepared, it has been found that even a dilute skim milk solution as low as 0.02% by weight, not considered to have the blocking action in the prior art, has the action of enabling a sufficient lowering of nonspecific reactions, and it has been confirmed also that the specific reactivity will not be lowered substantially at that skim milk concentration, whereby a high sensitivity immunoassay is obtained.

The reason why the assaying method of the present invention does not lower substantially the specific immunoreactivity is as follows.

That is, since particles of water soluble skim milk surrounded the antigen and antibody in the prior art, the antibody cannot approach the antigen, resulting in a lowering of the specific immunoreaction. But, by forming skim milk into a dilute aqueous solution and using the ultrasonic wave, skim milk in a completely dissolved state can be prepared. When an immunoreaction is carried out by using such a skim milk solution, the skim milk in a completely dissolved state will not interfere with the antigen-antibody reaction. Moreover, it has been confirmed that nonspecific reactions are inhibited sufficiently at that concentration.

By using the method of the present invention, various antigens can be determined. Examples of such antigens include coagulated plasmin factors such as $\alpha_2$ plasmin-inhibitor ($\alpha_2$PI), $\alpha_2$PI-plasmin complex, protein C, protein S, lung-surfactant apoprotein, and tumor markers such as AFP and CEA.

As the antibody to be used in assaying various antigens as mentioned above, use can be made of polyclonal antibodies, monoclonal antibodies to those antigens, fragments thereof, such as F(ab')$_2$, Fab', Fab, and Facb, as the labelled antibody or fixed antibody. Among the above, use of a monoclonal antibody as the antibody is preferable, because a higher specificity assay is obtained, and the use of Fab' also is preferable because higher sensitivity is obtained.

Such polyclonal antibodies, monoclonal antibodies and fragments thereof can be obtained by known methods, for example, "Continued Biochemical Experimental Course" edited by Biochemical Society of Japan, vol. 5, p. 1–10, Tokyo Kagaku Dojin, 1986, the cell fusion method by Köhler and Milstein (G. Köhler and Milstein, *Nature* (London), 256, 495–497, (1975); and the methods of A. Nisonoff et al. and P. Parham (A. Nisonoff et al., *Arch. Biochem. Biophys.*, 89, 23 (1960); P. Parham, *J. Immunol.*, 131, 2895 (1983)).

Of such monoclonal antibodies, as the anti-human protein S monoclonal antibody, for example, (a) a monoclonal antibody to human protein S which specifically recognizes the conjugate of human protein S and c4B bound protein of human complement system control factor bound thereto, and (b) a monoclonal antibody to human protein S which selectively recognizes free human protein S, but does not recognize the conjugate of human protein S and the c4B bound protein of the human complement system control factor, as described in detail in the patent application (Japanese Unexamined Patent Publication (Kokai) No. 63-148994) of Japanese Patent application No. 61-296766 (filed on Dec. 15, 1986, entitled Monoclonal Antibody, Hybridoma, Method for Preparation of Monoclonal antibody, Method for Separating Human Protein S") may be included.

As the antigen-antibody reaction, there may be employed immunological assaying methods known in the art, such as the sandwich method using two kinds of antibodies recognizing the respectively different antigenic determinant sites of the antigen, or the two antibody method, but preferably the sandwich method is employed.

EXAMPLES

The present invention now will be illustrated further by, but is by no means limited to, the following Examples. In the following Examples, all percentages are by weight unless otherwise specified.

Example 1

Study of Solubility of Skim Milk and Maintenance of Dissolved State

Various concentrations of aqueous skim milk solutions (2.0, 1.5, 1.0, 0.8, 0.7, 0.6, 0.5, 0.4, 0.3, 0.2, 0.1, 0.05, 0.02, 0.01%) were mixed at room temperature using a stir rubber and then subjected to ultrasonication for 10 minutes for dissolution. To those various solutions were added thimerosal to a concentration of 0.01%. The solutions were stored in a refrigerator for 12 months, then a comparison was made of the protein at the start of the storage and that of the solutions stored for 12 months. A Bradford protein test kit was used to examine the extent of the maintenance of the state of dissolution at the various concentrations. FIG. 1 shows the rate of maintenance of the state of dissolution at the various concentrations (%). In FIG. 1, the following formula was used:

Rate of maintenance of state of dissolution (%) =

(Amount of protein after 12 months/

Amount of protein at start of storage) × 100

As shown in FIG. 1, if the concentration of the skim milk is less than 0.8%, the solution can be stored stably in the dissolved state.

Example 2

Figure 2:
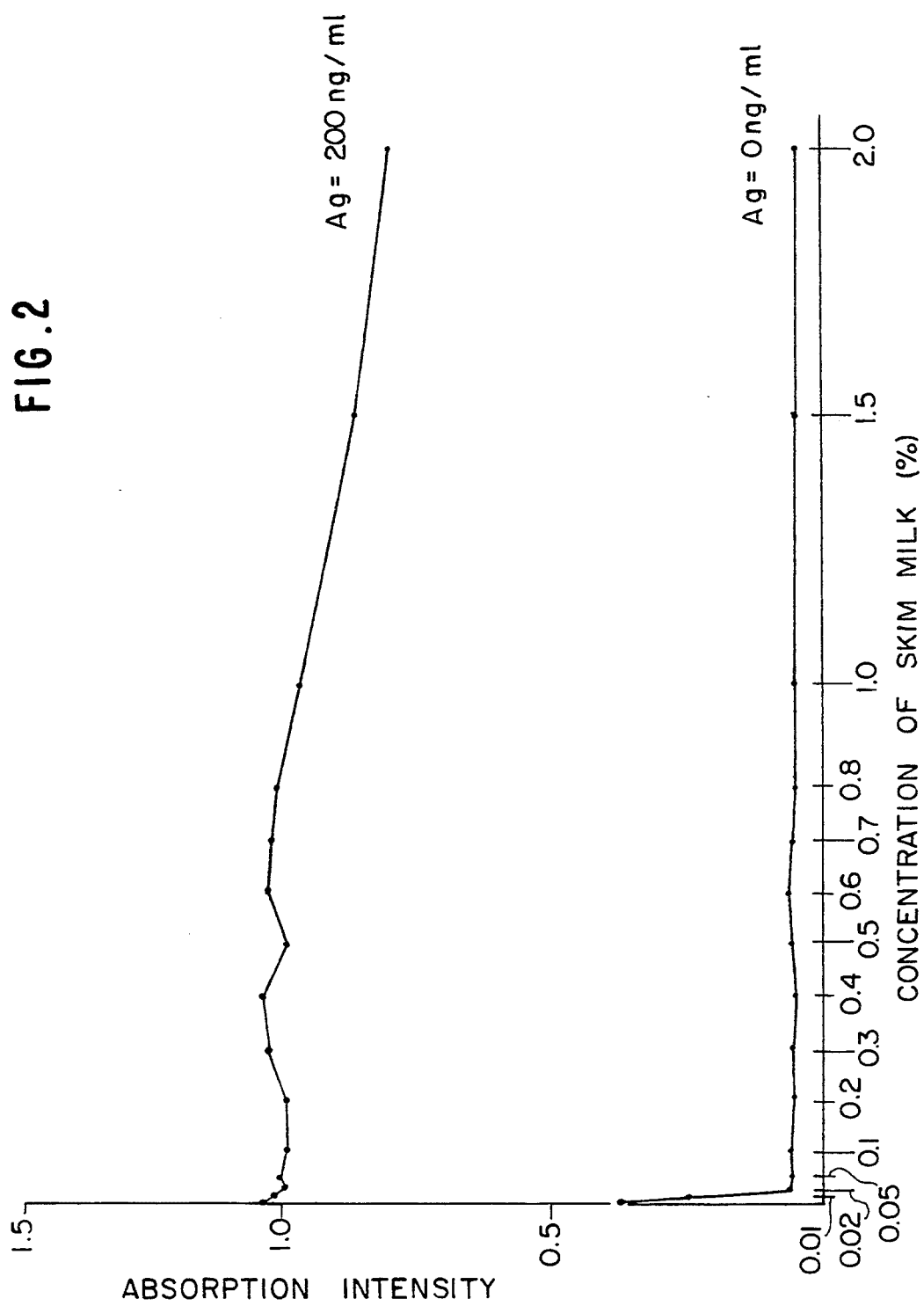
FIG. 2 shows concentration of skim milk in the $\alpha_2$PI-plasmin conjugate measurement system and the effects of the addition thereof.

Study of Dependence on Concentration of Skim Milk of Specific Reactivity and Nonspecific Reactivity in Immunoassay of $\alpha_2$ PI-Plasmin Complex The skim milk solutions of Example 1 were used for an immunoassay of 0, 50, 100 and 200 ng/ml of $\alpha_2$ PI-plasmin complexes. The measurement values of the nonspecific reactions (Ag=0) and the specific reaction (Ag=200 ng/ml) were compared with solutions without skim milk added. The results were as shown in FIG. 2. When the skim milk amount is less than 0.02%, a rise was observed in the immunologically nonspecific reactions. Further, when the skim milk amount was over 0.8%, the specific reaction began to be inhibited. Therefore, it was confirmed that a skim milk concentration of 0.02 to 0.8% is most suitable for performing an immunoreaction in a solution with a high sensitivity.

Example 3

Immunoassay of $\alpha_2$-Plasmin Inhibitor ($\alpha_2$ PI)

Figure 3:
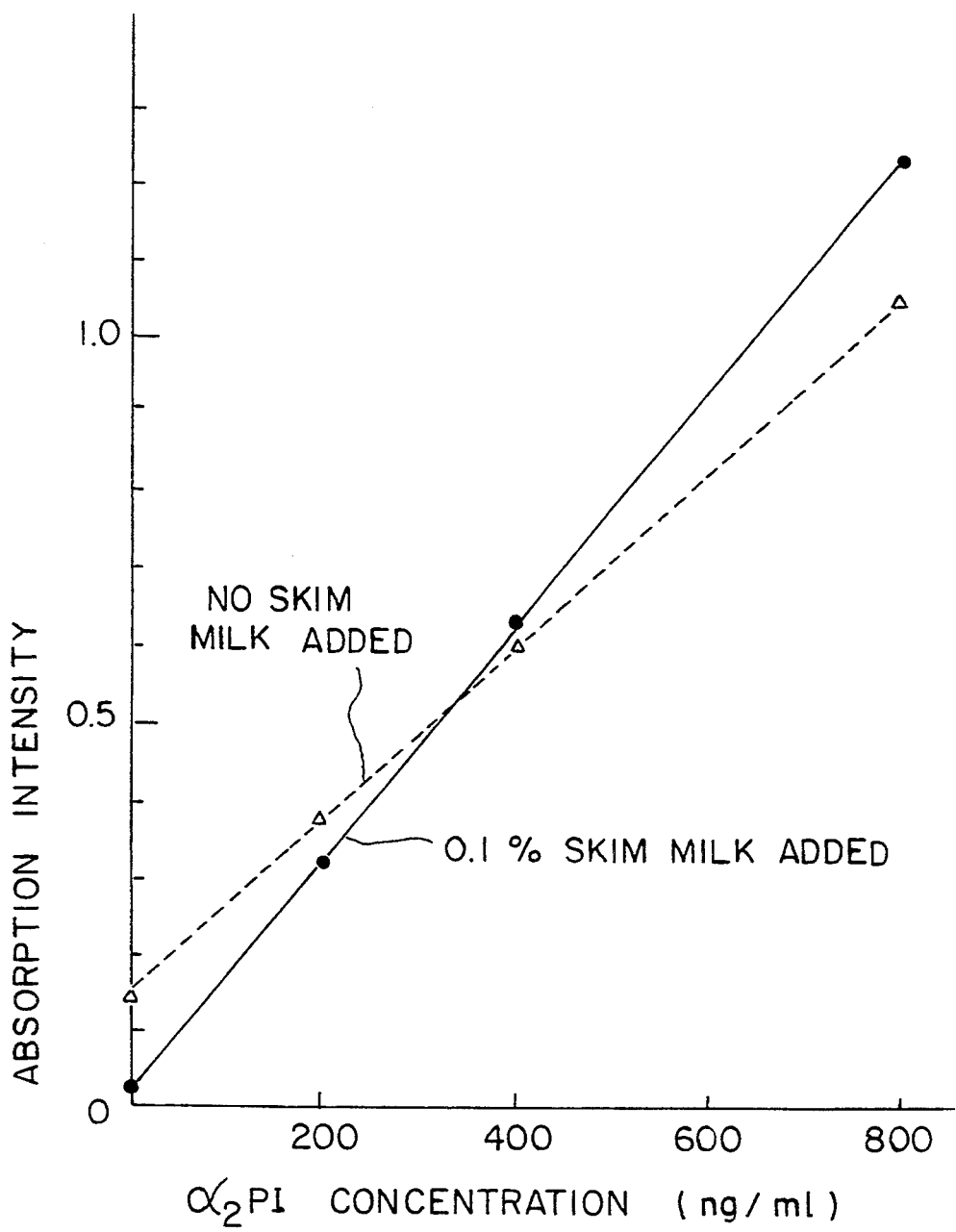
FIG. 3 and FIG. 4 show the calibration curves wherein the skim milk effects in the $\alpha_2$PI and protein C measurement systems, respectively, are compared when skim milk is not added.

Polystyrene balls (diameter of 6 mm) immobilizing monoclonal antibodies for human $\alpha_2$ plasmin inhibitor ($\alpha_2$ PI ) and a peroxidase labeled anti-human $\alpha_2$ PI-monoclonal antibody recognizing different epitopes on the $\alpha_2$ PI molecule were used. In a 0.01M phosphate buffered physiological saline solution (pH 7.4) including 0.5% BSA and 0.1% skim milk, reactions were performed at a temperature of 37° C. for 60 minutes on the levels of a human $\alpha_2$ PI concentration of 0, 200, 400 and 800 ng/ml, then the balls and reaction liquid were separated and the balls were washed thoroughly with the physiological saline solution. Next, a reaction was caused in an aqueous solution containing a tetramethylbenzidine-$H_2O_2$ color forming system, then a reaction stopper was added to stop the oxidation reaction, the absorption strength at a wavelength of 650 nm was measured, and the concentration and absorption strength were plotted to obtain a calibration curve. That was compared with a calibration curve prepared by the same method as above except that the 0.1% skim milk was omitted, whereupon, as shown in FIG. 3, in the assay system where 0.1% skim milk was added, the absorption strength of human $\alpha_2$ PI concentration 0 ng/ml was lower and the nonspecific reactions was reduced compared with the system where skim milk was not added.

Example 4

Immunoassay of Protein C

Figure 4:
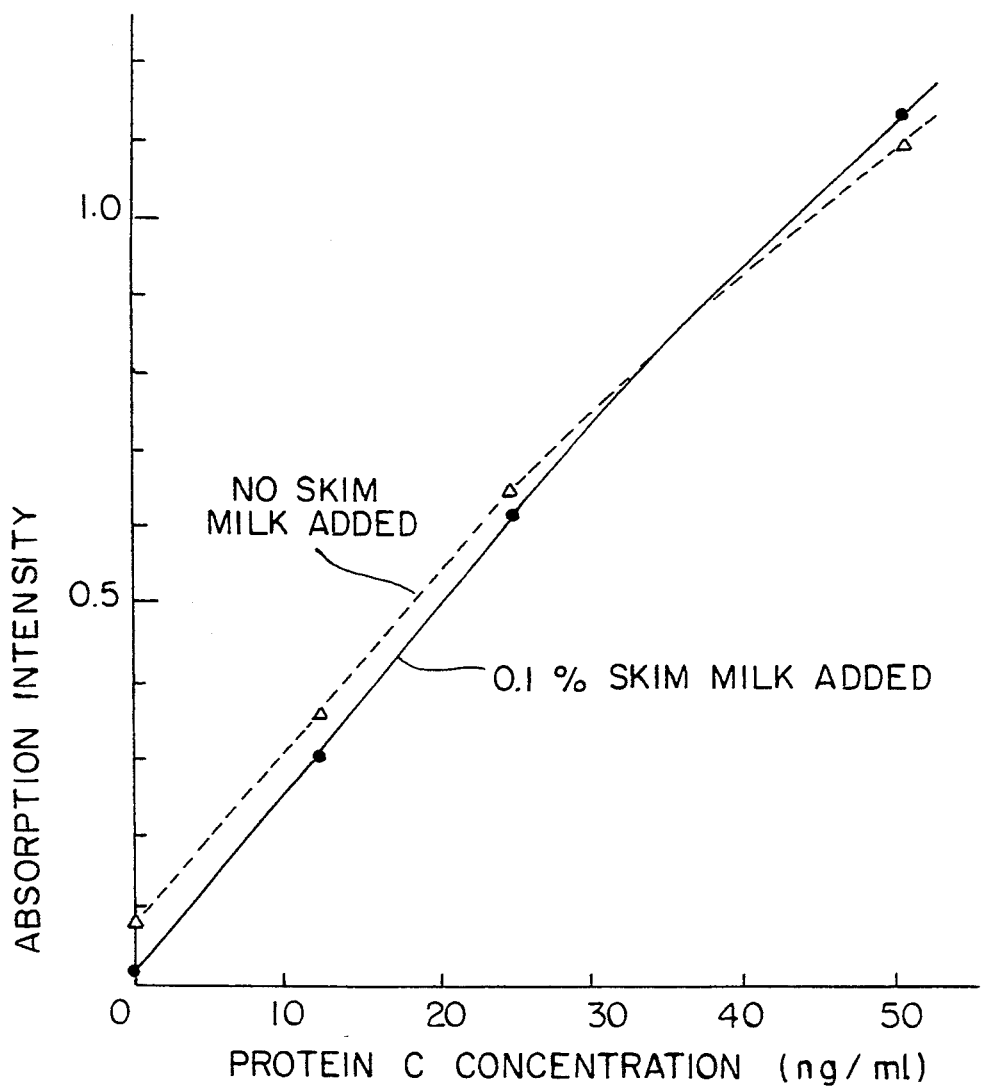

Polystyrene balls (diameter of 6 mm) immobilizing an anti-human protein C-monoclonal antibody for the Gla domain of human protein C and a peroxidase labeled anti-human protein C-monoclonal antibody recognizing a different epitope from the monoclonal antibody were used. A reaction was performed in a 0.05M tris buffered saline solution (pH 7.4) including 0.5% BSA, 0.1% skim milk, 5 mM calcium chloride, and 1 U/ml heparin on levels of concentration of a protein C of 0, 12.5, 25, and 50 ng/ml at 37° C. for 30 minutes, then the balls and reaction liquid were separated and the balls thoroughly washed. Next, a color was brought out by a tetramethylbenzidine-$H_2O_2$ color formation system, then a reaction stopper was added to stop the oxidation reaction, the absorption strength at a wavelength of 650 nm was measured, and the concentration and absorption strength were plotted to obtain a calibration curve. That was compared with a calibration curve prepared by performing a reaction by the same method as above except that the 0.1% skim milk was omitted, whereupon it was found that, as shown in FIG. 4, with the assay system with 0.1% skim milk added, the absorption strength of a protein C concentration of 0 ng/ml was lower and the nonspecific reaction was reduced than with a system with no skim milk added.

Reference Example 1

Production and Purification of Human Protein S (PS) Monoclonal Antibody

Purified human PS was used for immunization of two female Balb/C mice (4 week old) four times at 14 day intervals. In the first immunization, the PS was dissolved in PBS. A 50 μg amount of human PS was mixed with a suitable amount of Complete Freund's Adjuvant and the emulsion of the same was administered intraperitoneally (0.5 mg/head). In the second and third immunizations, the same 50 μg of human PS was mixed with Freund's Incomplete Adjuvant and similarly administered intraperitoneally. In the final immunization, 30 μg of human PS was additionally administered as it was in a PBS solution from the mouse caudal veins. Three days after the final immunization, the spleen cells of the immunized mice were used for cell fusion.

The spleen cells of the immunized mice were mixed with myeloma cells (P3U1) of mice of the same strain in ratios of about 2:1 to about 15:1 and cell fusion was performed by the method of Köhler and Milstein using 50% polyethylene glycol 1540 (made by Wako Junyaku) as the fusion promoter. After fusion, the cells were suspended in a 10% FCS°-RPMI-1640 medium for a cell concentration of $1 \times 10^6$ cells/ml and were divided into 100 μl portions per well in a 96 well microplate (Coster).

The fused cells were incubated in a $CO_2$ incubator (5% $CO_2$, 37° C.), the medium changed to a medium containing hypoxanthine, aminopterin, and thymidine (HAT medium) grown in the HAT medium, and subjected to screening for the spleen cells and the hybridoma from the myeloma cells.

The antibodies in the incubated supernatant of the hybridoma were detected by the ELISA method using microtiter plates coated with antigen human PS. For the second antibody, alkaline phosphatase labelled rabbit anti-mouse IgG antibody was used and the bonding with antigen PS was studied. Out of the total of 494 wells plated with fused cells, a formation of colonies was observed in 487 wells, among which were 94 antibody producing positive wells showing bonding with antigen PS.

Cloning by the limited dilution method was repeated twice for four of the wells of those antibody producing positive wells and six clones were obtained. The obtained clones were suspended in 90% FCS - 10% DMSO and stored in liquid nitrogen.

The monoclonal antibodies produced by the clones were proliferated of the abdominal cavities in Balb/C mice and purified from the ascites using protein A-Sepharose 4B columns.

TABLE 1

| | (Cell Fusion) | | |
|---|---|---|---|
| | Cell fusion 1 | Cell fusion 2 | Total |
| Spleen cells (cells/ml) | $1.15 \times 10^7$ | $6.70 \times 10^6$ | |
| Myeloma cells (cells/ml) | $1.72 \times 10^6$ | $1.33 \times 10^6$ | |
| Ratio of spleen cells/ myeloma cells | 6.6 | 5.0 | |
| Cell count (cells/well) | $0.57 \times 10^5$ | $0.67 \times 10^5$ | |
| No. of wells | 302 | 192 | 494 |
| Colony formation positive wells | 298 (98.6%) | 189 (98.4%) | 487 (98.6%) |
| Antibody production positive wells showing bonding with protein S | 66 (21.8%) | 28 (14.8%) | 94 (19.0%) |

Reference Example 2

Properties of Purified Monoclonal Antibodies

A study was made of the IgG of the various clones purified from the mouse ascites with respect to the classes and binding ability with human protein S.

The classes of the mouse monoclonal antibodies were determined by the Ouchterlony method using anti-mouse antisera specific to the individual classes.

The results are shown in Table 2.

The binding affinity with human protein S was evaluated by reaction between human protein S on a solid phase on microtiter plates and monoclonal antibodies diluted for a suitable concentration and detection by alkaline phosphatase labelled goat anti-mouse IgG and as a result, it was found that the strength of the bonds of the six types of monoclonal antibodies with human protein S were 2B9F12≅2B9C10>3C3G8>3C4G4>2B9G3>>2E12C7.

TABLE 2

| Classes of Monoclonal Antibodies | |
|---|---|
| Antibody name | Class |
| 2B9F12 | $IgG_1$ |
| 2B9C10 | $IgG_1$ |
| 3C3G8 | $IgG_3$ |
| 3C4G4 | $IgG_1$ |
| 2B9G3 | $IgG_1$ |
| 2E12C7 | $IgG_1$ |

Reference Example 3

Reactivity with Human C4bp-Protein S Complex

The above-mentioned six types of purified monoclonal antibodies were coated on microtiter plates at a concentration of 10 μg/ml, blocked with 1% BSA, then reacted with normal human plasma diluted to suitable concentrations and caused between the C4bp-protein S complexes in the plasma and the monoclonal antibodies. Next, an alkaline phosphatase labelled anti-C4bp antibody was added and the binding ability of the six types of monoclonal antibodies with the C4bp-protein S complex was detected and studied.

As a result, it was shown that the monoclonal antibody 2E12C7 has an extremely weak binding ability with respect to the free protein S, but shows an advanced, specific binding ability with respect to the C4bp-protein S complex, and that the strength of the bonds of the six types of monoclonal antibodies with respect to the C4bp-protein S complex is 2E12C7>>2B9F12≅2B9C10>3C3G8>3C4G4>2B9G3.

As shown by reference examples 2 and 3, 2B9F12 and 2B9C10 are obtained as monoclonal antibodies which do not recognize the complex of C4bp and protein S but specifically recognize and bond with free human protein S.

Example 5

(1) Preparation of Antibody Immobilizing Beads

Polystyrene beads (diameter of 6 mm) were allowed to stand one day and night in a 0.01M phosphate buffered saline solution (PBS) (pH 7.4) having a concentration of goat anti-human-protein S antibody (polyclonal antibody, made by American Diagnostica Co.) of 20 μg/ml at a temperature of 4° C., were washed with PBS and then were allowed to stand one day and night in an aqueous solution of 0.5% bovine serum albumin (BSA) at a temperature of 4° C. to obtain antibody immobilized beads.

(2) Preparation of Horseradish Peroxidase labelled Monoclonal Antibody

To a PBS solution of 1.0 mg/ml of monoclonal antibody (2B9F12) specifically recognizing free human protein S, 50 μl of a dimethyl formamide solution of 10 mg/ml of N-(m-maleimide benzoate)-N-succinimido ester (MBS) were added, which then was reacted at a temperature of 25° C. for 30 minutes. Then a column packed with Sephadex G-25 was used and gel filtration was performed with a 0.1M phosphate buffered solution (pH 6.0) to separate the MBS acylated monoclonal antibodies and the unreacted MBS.

On the other hand, to 2.0 ml of a PBS solution of 1.0 mg/ml of horseradish peroxidase (HRP) was added a 10 mg/ml ethanol solution of N-succinimidyl-3-(2-pyridyl-thio)propionate (SPDP), which then was reacted at 25° C. for 30 minutes. Then a column packed with Sephadex G-25 was used and gel filtration performed with 0.01M acetic acid buffer solution (pH 4.5) for purification. The fraction containing the pyridyldisulfide group substituted HRP was taken and concentrated about 10 fold under ice cooling in a collodion bag and then 1 ml of a 0.1M acetic acid buffer solution (pH 4.5) containing 0.85% of NaCl and 0.1M dithiothreitol was added thereto. The whole was agitated at 25° C. for 30 minutes and the pyridyldisulfide group substituted HRP molecules were reduced, then a Sephadex G-25 column was used for gel filtration by 0.1M phosphate buffered solution (pH 6.0) to obtain a fraction containing the thiol group substituted HRP.

Next, the obtained MBS acylated monoclonal antibodies and thiol group substituted HRP were mixed and a collodion bag was used for concentration under ice cooling to a 4 mg/ml protein concentration. The whole was allowed to stand one day and night at 4° C., then a column packed with Ultrogel AcA44 (made by LKB Co., France) was used for gel filtration by PBS, whereupon an HRP labelled monoclonal antibody was obtained.

(3) Assay of Human Protein S

One bead each immobilizing goat anti-human protein S antibodies, 200 μl portions of a PBS solution (pH 7.4) containing 0.1% BSA containing purified human protein S in various concentration of 0, 50, 100, 200 and 400 ng/ml and 0.1% skim milk, and 200 μl portions of a PBS solution (pH 7.4) containing HRP labelled monoclonal antibodies and containing 0.1% BSA and 0.1% skim milk were added respectively to test tubes (n=2) and incubated at a temperature of 37° C. for one hour.

Next, the solutions in the test tubes were removed by suction, then the test tubes were washed two times with PBS. Next, 400 μl portions of 0.1M phosphate - citrate buffered solution (pH 4.0) containing 0.02% of tetramethylbenzidine hydrochloride and 0.005% of hydrogen peroxide were added to the test tubes, were incubated at a temperature of 37° C. for 30 minutes and then 1 ml portions of an aqueous solution containing 0.1% NaF and 2% acetic acid were added as reaction stoppers to stop the enzymatic reaction.

Figure 5:
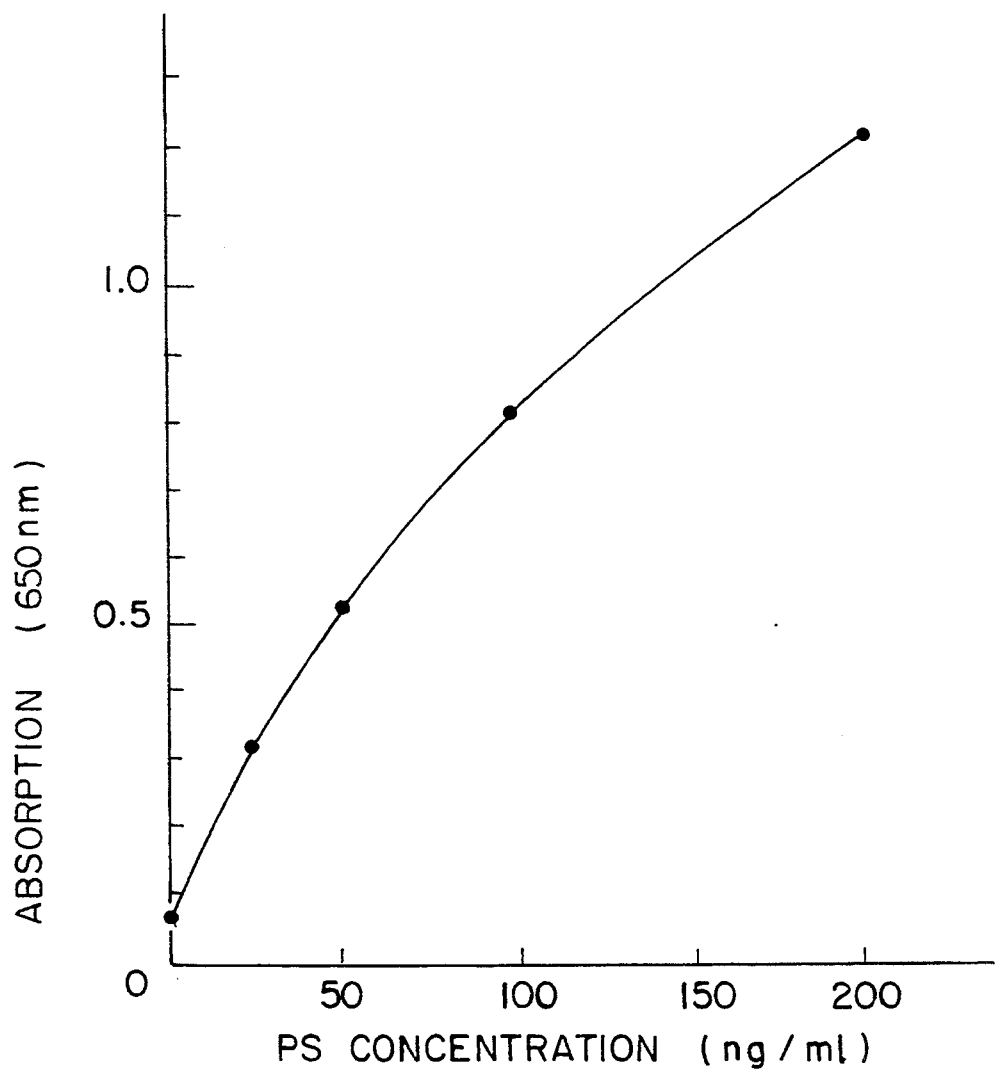
FIG. 5 shows the calibration curve for an immunological assay of human protein S according to the present assay (Example 5), when 0.5% by weight of skim milk is added to the immunoreaction solution.

Next, the solutions were measured to obtain the absorption strength of a wavelength of 650 nm using a spectrophotometer. The results were plotted with the concentration of human protein S, whereby a calibration curve for assay of the concentration of human protein S having a concentration dependence was obtained (see FIG. 5).

As an assay of the concentration of human protein S in a plasma specimen, 200 μl of a solution of normal mixed human plasma diluted 50 fold by a PBS solution (pH 7.4) containing 0.1% BSA and 0.1% skim milk were added to a test tube together with antibody immobilized beads and 200 μl of an HRP labelled monoclonal antibody solution. An immunoreaction and color formation reaction were performed by the same method as used for preparing the calibration curve, then the absorption was measured by a spectrophotometer and the concentration of human protein S was found and converted to the concentration in the plasma using the calibration curve. The result was a 10.4 μg/ml concentration in the plasma.

Comparative Example 1

One bead each immobilizing goat anti-human protein S antibodies prepared in the same way as in Example 1, 200 μl portions of a PBS solution (pH 7.4) containing 0.5% BSA containing purified human protein S in various concentrations of 0, 50, 100, 200 and 400 ng/ml, and 200 μl portions of a PBS solution (pH 7.4) containing 0.5 percent BSA and HRP labelled mouse anti-human protein S-monoclonal antibodies prepared in the same way as Example 1 were added respectively to test tubes (n=2) and incubated at a temperature of 37° C. for one hour.

Next, the solutions in the test tubes were removed by suction, then the test tubes were washed two times with PBS. Next, 400 μl portions of 0.1M phosphoric acid - citric acid buffer solution (pH 4.0) containing 0.02% of tetramethylbenzidine hydrochloride and 0.005% of hydrogen peroxide were added to the test tubes. The tubes were incubated at a temperature of 37° C. for 30 minutes, then 1 ml portions of an aqueous solution containing 0.1% NaF and 2% acetic acid were added as reaction stoppers to stop the oxidation reaction.

Figure 6:
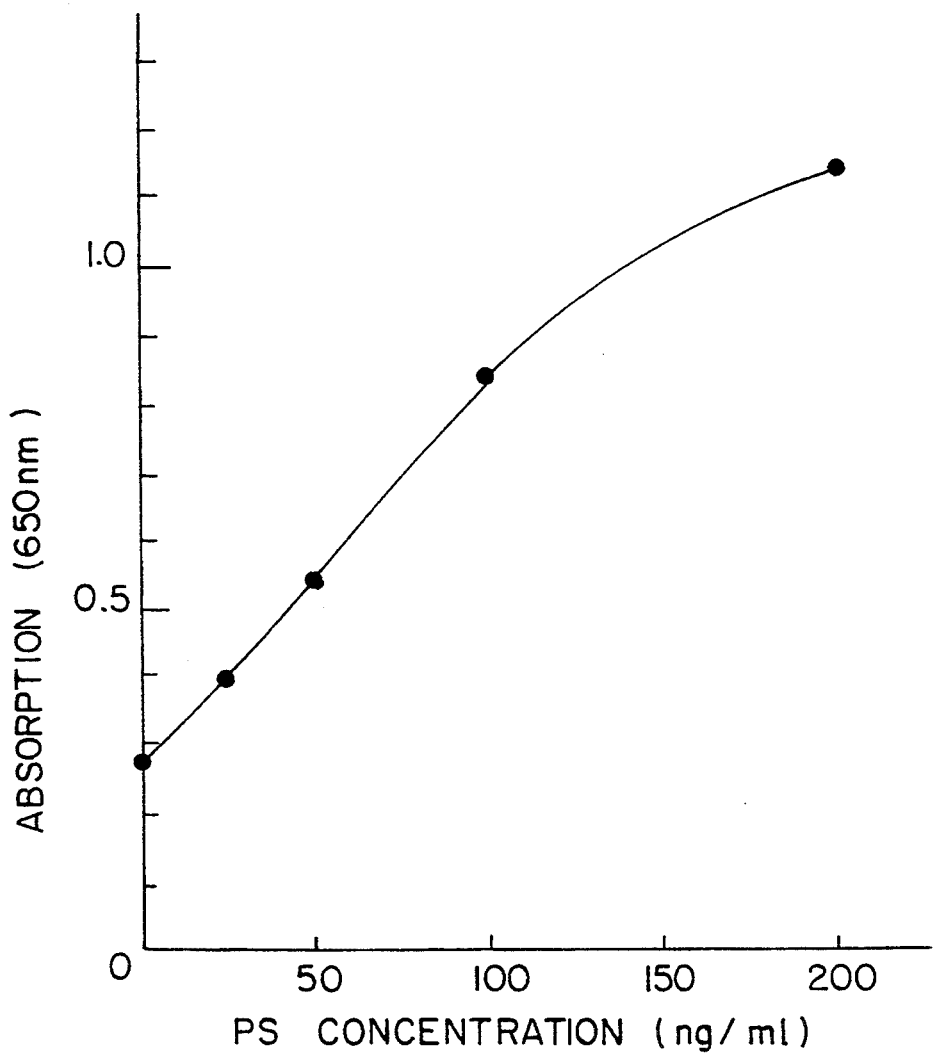
FIG. 6 shows the calibration curve for an immunological assay of human protein S when skim milk is not added to the immunoreaction system (Comparative Example 2)

Next, the solutions were measured to obtain the absorption strength of a wavelength of 650 nm using a spectrophotometer. The results were plotted with the concentration of human protein S, whereby a calibration curve for assay of the concentration of human protein S having a concentration dependence was obtained (see FIG. 6).

Due to the nonspecific reactions, the calibration curve had a base line of an absorption strength of 0.28, which is extremely high, a good sensitivity could not be obtained and the results were unsatisfactory for an assay system.

Comparative Example 2

One bead each immobilizing goat anti-human protein S antibodies prepared in the same way as in Example 5, 200 μl portions of a PBS solution (pH 7.4) containing 0.5% BSA and purified human protein S in various concentrations of 0, 50, 100, 200 and 400 ng/ml and 2% skim milk, and 200 μl portions of a PBS solution (pH 7.4) containing 0.5% BSA and HRP labelled mouse anti-human protein S-monoclonal antibodies prepared in the same way as Example 5 and 2% skim milk were added respectively to test tubes (n=2) and incubated at a temperature of 37° C. for one hour.

Next, a color formation reaction and reaction stopping were performed by the same method as in Example 5, then the solutions were measured to obtain the absorption strength of a wavelength of 650 nm using a spectrophotometer. The results were plotted with the concentration of human protein S, whereby a good calibration curve having the same type of concentration dependence as in the case of Example 5 was obtained.

However, when the immunoreaction buffer solution comprised of a PBS solution (pH 7.4) containing 0.5% BSA and 2% skim milk and a PBS solution (pH 7.4) containing HRP labelled monoclonal antibodies and 0.5% BSA and 2% skim milk were filled in vials in a sterile state and stored in a refrigerator for one month, the skim milk in the solutions formed coagulated masses.

The coagulated masses were separated out and the immunological assay performed. It was not possible to obtain a calibration curve having a concentration dependence and an assay could not be performed.

Example 6

Skim milk addition effect in human placenta derived acidic glutathione S-transferase measurement system In a buffer for immunoassay (1% bovine serum albumin, 0.01M phosphate buffer, 0.85% NaCl buffer, pH 7.2), 0, 25 and 50 μg/ml solutions of acidic glutathione S-transferase derived from human placenta (hereinafter referred to as acidic GST derived from human placenta) were prepared, and each 100 μl thereof, 100 μl of the solution containing skim milk in the buffer for immunoassay (1% bovine serum albumin, 0.01M phosphate buffer, 0.85% NaCl buffer, pH 7.2) as mentioned above controlled to the final concentration of 0, 0.05, 0.1 and 0.2%, and 200 μl of the buffer for immunoassay (1% bovine serum albumin, 0.01M phosphate buffer, 0.85% NaCl buffer, pH 7.2) as mentioned above containing the anti-acidic GST derived from human placenta monoclonal antibody labelled with horseradish peroxides were placed in a test tube and well mixed. To the mixture in each test tube was placed one bead having the rabbit anti-acidic GST derived from human placenta polyclonal antibody, and incubated at 37° C. for 2 hours. Then, after the solution within the test tube was removed by suction, the bead was washed with 2 ml of physiological saline for 3 times, and then to each 0.4 ml of 0.1M phosphate-citrate buffer (pH 4.0) containing 0.02% 3,3',5'5'-tetramethylbenzidine hydrochloride and 2.5 mM $H_2O_2$ were added into each test tube to carry out incubation at 37° C. or 30 minutes, followed by addition to each of 1 ml of 1N aqueous sulfuric acid as the reaction stopping agent to stop the enzymatic reaction.

Figure 7:
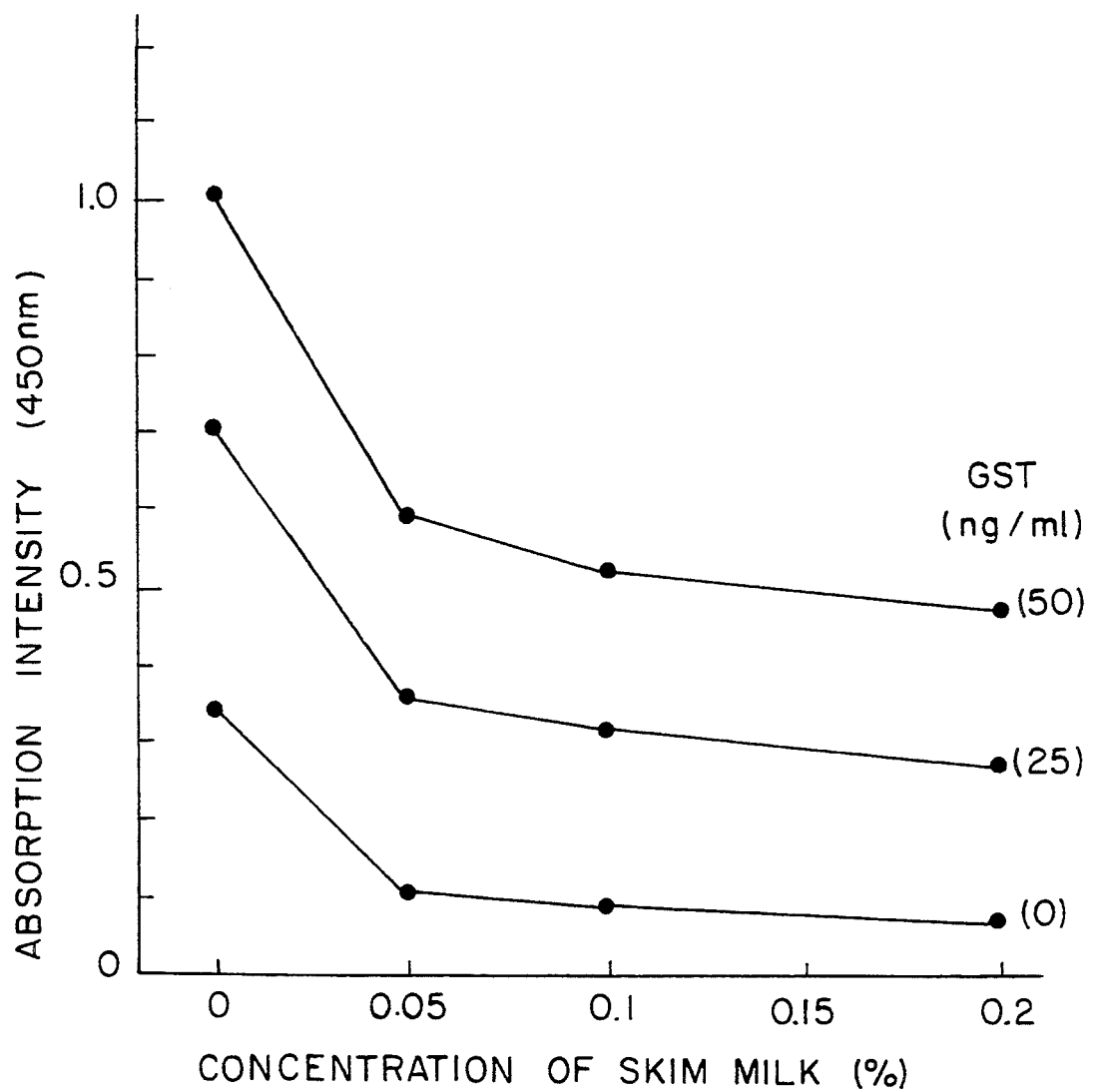
FIG. 7 shows the influence on the immunoreaction of the concentration of skim milk added to the acidic GST measurement system derived from human placenta.

Subsequently, the solutions were subjected to measurement of absorption intensity at 450 nm with purified water as the reference by using a spectrophotometer, and the results are shown in FIG. 7.

Example 7

Skim milk addition test in the chondrocalcin measurement system

Figure 8:
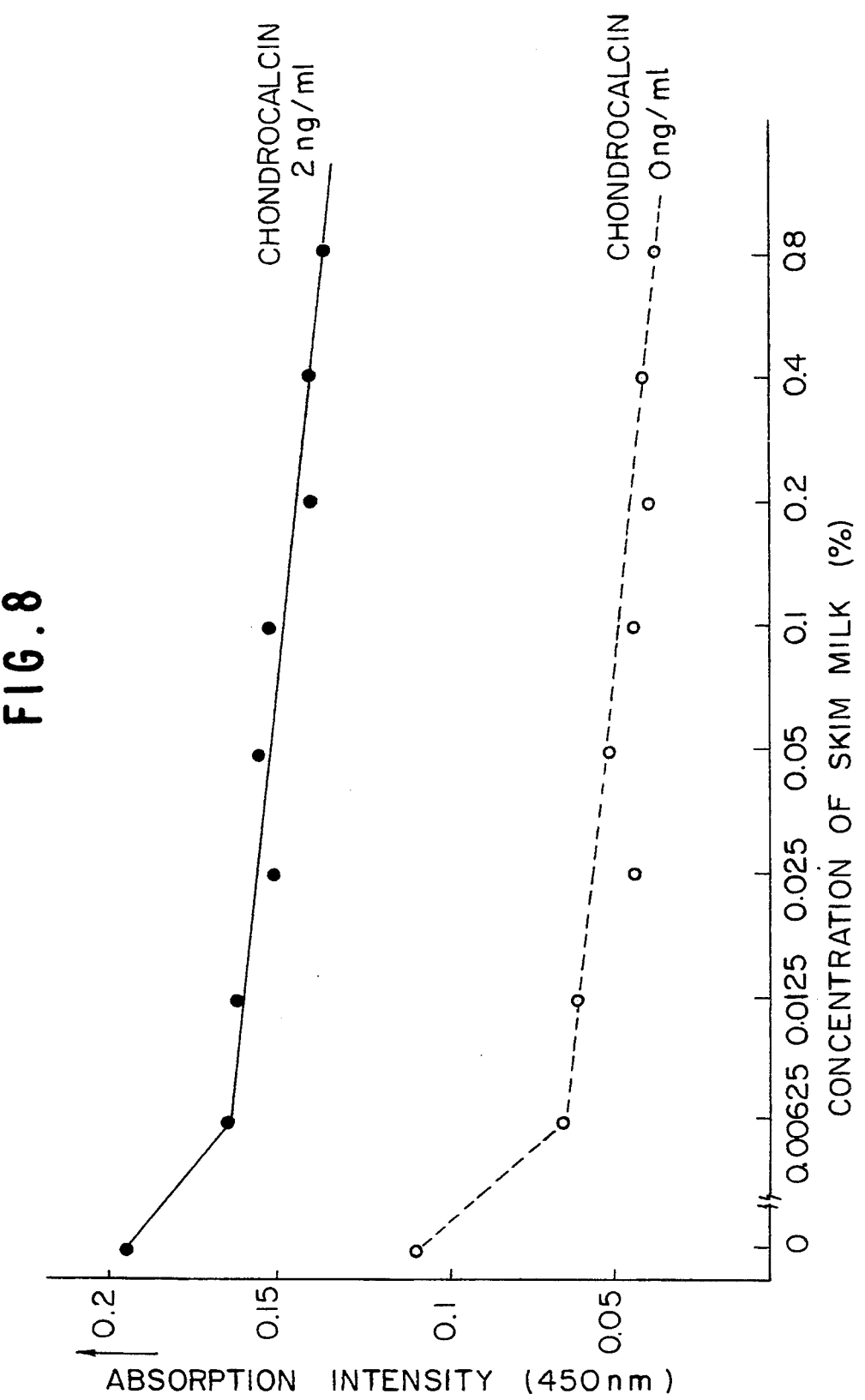
FIG. 8 shows the influence on the immunoreaction of the concentration of skim milk added to the chondrocalcin measurement system.

Bovine chondrocalcin was diluted with a buffer for immunoassay (1% bovine serum 0.01% phosphate, 0.85% NaCl buffer pH=7.2 containing 1% bovine serum, albumin, hereinafter abbreviated as 1% BSA-PBS) to prepare a 0, 2 ng/ml solution, and 50 μl thereof and 50 μl of a solution containing skim milk in the buffer for immunoassay (1% bovine serum, 0.01% phosphate, 0.85% NaCl buffer pH=7.2 containing 1% bovine serum alumin) as mentioned above controlled to the final concentrations of 0, 0.00625, 0.0125, 0.025, 0.05, 0.1, 0.2 and 0.8% were mixed well. In the microplate having the rabbit anti-bovine chondrocalcin polyclonal antibody fixed thereon, 100 μl of each of the above solutions were placed, followed by incubation at 37° C. for 2 hours (primary incubation). Then, after the mixture was washed with PBS-0.05% Tween-20, Fab' of the anti-bovine chondrocalcin polyclonal antibody labelled with peroxidase in 100 μl of the dilutions were placed in each well to carry out the incubation at 37° C. for one hour (secondary incubation). After washed with PBS-0.05% Tween-20, 100 μl of a substrate solution for peroxidase (containing 2.5 mM $H_2O_2$, 0.0225%, 3,3',5,5'-tetramethylbenzidine) were added to effect color formation at 37° C. for 0.5 hours and the reaction was stopped with addition of 25 μl of 1N-aqueous sulfuric acid, followed by measurement of the absorption intensity by a plate reader at 450 nm. The results are shown in FIG. 8. As apparent from that Figure, nonspecific adsorption can be prevented at a skim milk concentration of 0.00625% or higher.

Example 8

Skim milk addition test in the IgA-IC (IgA class immunocomplex) measurement system A standard substance (IgA-C3) at a concentration of 1, 25 and 50 μg/ml was diluted with a buffer for immunoassay (0.5% bovine serum albumin, 0.01M phosphate, 0.85% NaCl buffer, pH 7.2, hereinafter abbreviated as 0.5% BSA-PBS), and 0.2 ml of each dilution was taken up in a test tube. Then, 0.2 ml of a skim milk containing solution controlled to the final concentration of 0, 0.05, 0.1 and 0.2% with 0.5% BSA-PBS were added and well mixed. Then, each bead having the rabbit anti-human C3 Facb fixed thereon was placed and the incubation was carried out at 37° C. for one hour (primary incubation). Subsequently, after the solution within the test tube was removed by suction, the bead was washed with 2 ml of physiological saline 3 times and thereafter to each were added 0.4 ml of a stock liquor of the goat anti-human IgA antibody (manufactured by Cappel) labelled with horseradish peroxidase diluted each 10,000-fold with 0.5% BSA-PBS solution containing 0, 0.05, 0.1 and 0.2% skim milk, followed by incubation at 37° C. for one hour (secondary incubation). Then, after the solution within the test tube was removed by suction, the bead was washed with 2 ml of physiological saline 3 times and thereafter to each were added 0.4 ml of 0.1M phosphate-citrate buffer (pH 4.5) containing 0.05% diammonium 2,2'-azinobis-(3-ethyl-6-benzthiazolinesulfonate) and 1 mM hydrogen peroxide to effect incubation at 37° C. for 30 minutes, followed by addition of 1 ml of 0.1M aqueous oxalic acid as the reaction stopping agent to stop the enzymatic reaction.

Figure 9:
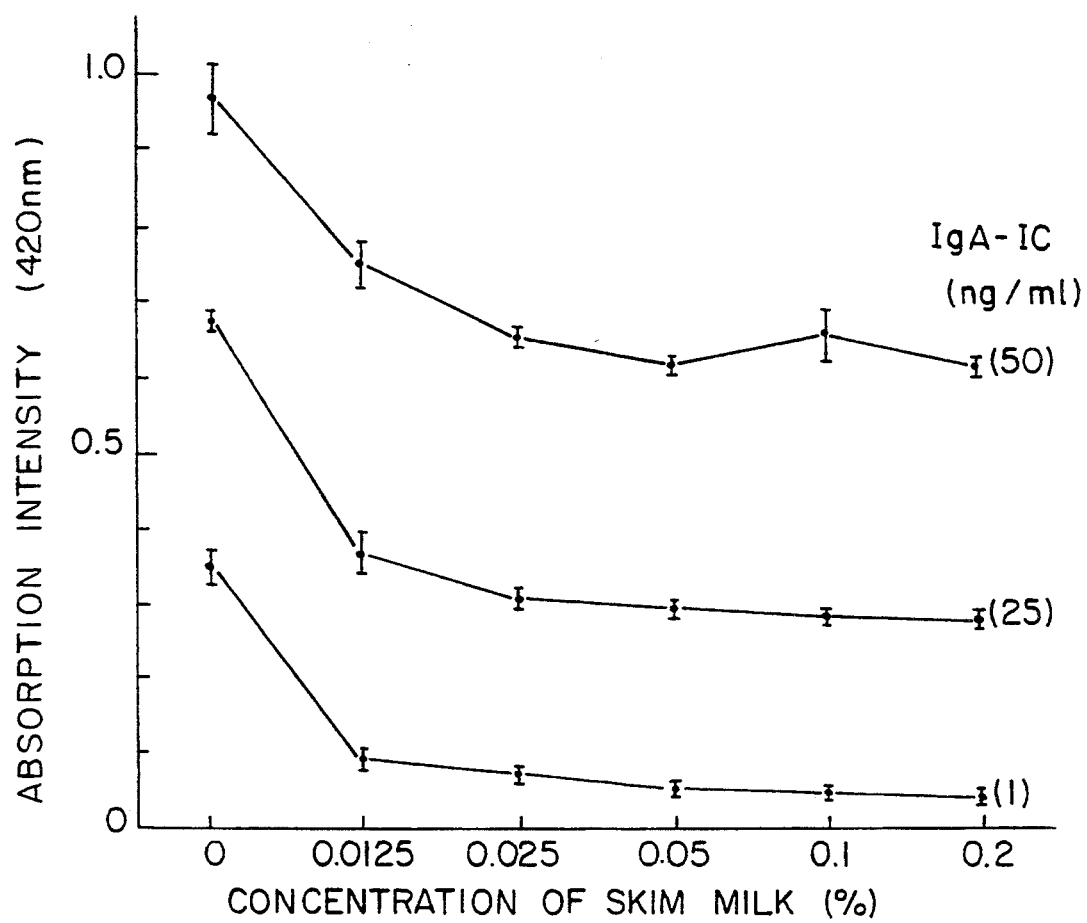
FIG. 9 shows the influence on the immunoreaction of the concentration of skim milk added to the IC measurement system.

Subsequently, the solutions were subjected to measurement of the absorption intensity at the wavelength of 420 nm with the reagent blank (by using of 0.5% BSA-PBS instead of the standard substance) as a control by use of a spectrophotometer, and the results are shown in FIG. 9.

Example 9

Influence of addition of various proteins on the nonspecific reaction (N)/specific reaction (S) ratio in immunoreaction Using balls (diameter 6 mm) having the polyclonal antibody to human plasminogen fixed thereon and the anti-human $a_2$ PI-monoclonal antibody labelled with peroxidase, in 0.01M phosphate buffer physiological saline (pH 7.4) containing 0.25% of various proteins of urease, gelatin, α-casein, β-casein, casein, skim milk, PFC (partial FC of IgG), NZ Case (pepsin decomposed product of casein), gelatin Hydrolysate Enzymatic-Acid, orosomucoid and ovoglycoprotein, incubation was carried out at 37° C. for 60 minutes for each level of human $a_2$ PI-plasmin conjugate concentration of 0, 100 ng/ml and then the balls and the reaction mixture were separated, followed by thorough washing of the balls with physiological saline. Then, the balls were permitted to react in an aqueous solution containing the color forming system of tetramethylbenzidine-$H_2O_2$ and thereafter, the enzymatic reaction was stopped by addition of a reaction stopping agent, followed by measurement of the absorption intensity at 650 nm wavelength.

Figure 10:
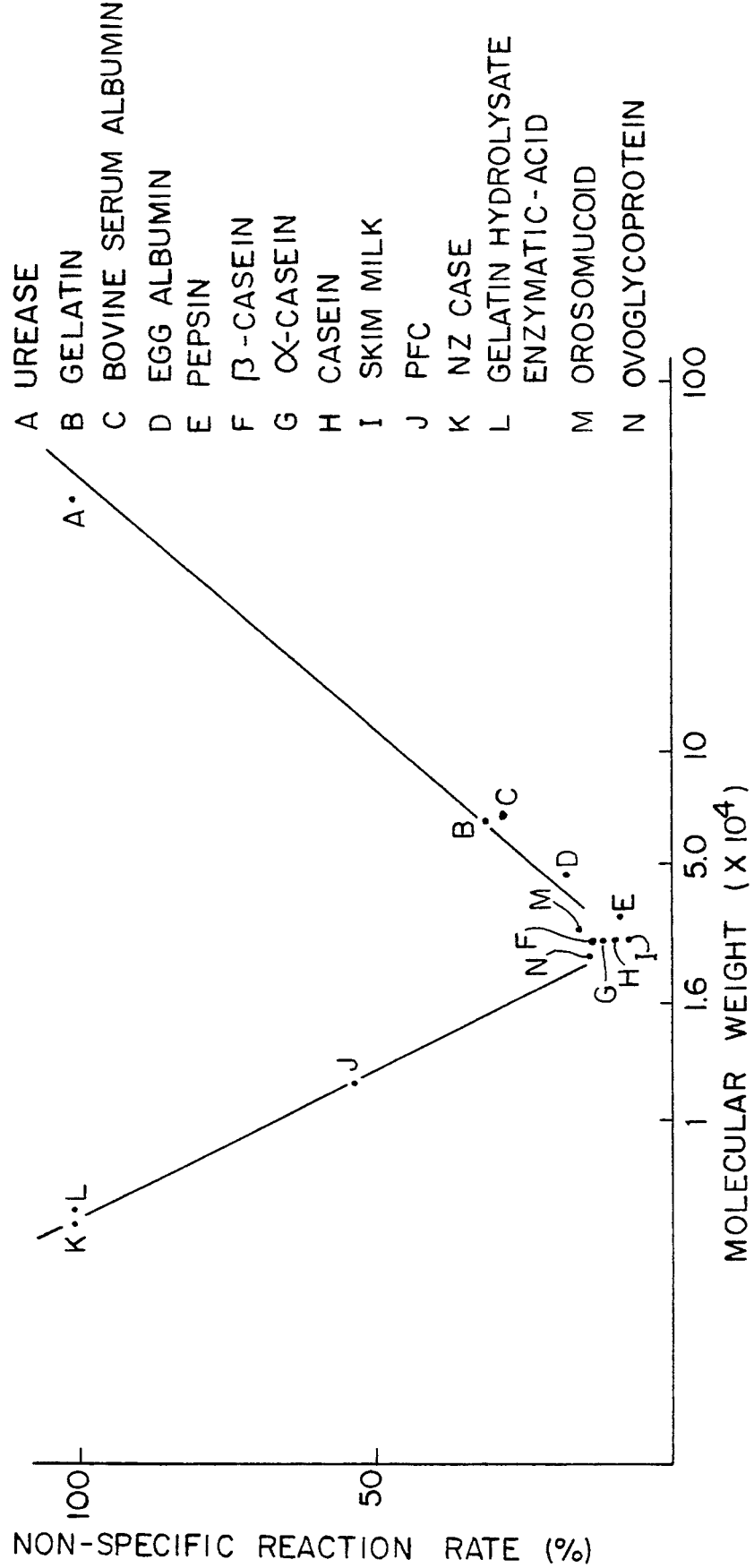
FIG. 10 shows the correlation between the nonspecific reaction rate and molecular weights of various proteins.
Figure 11:
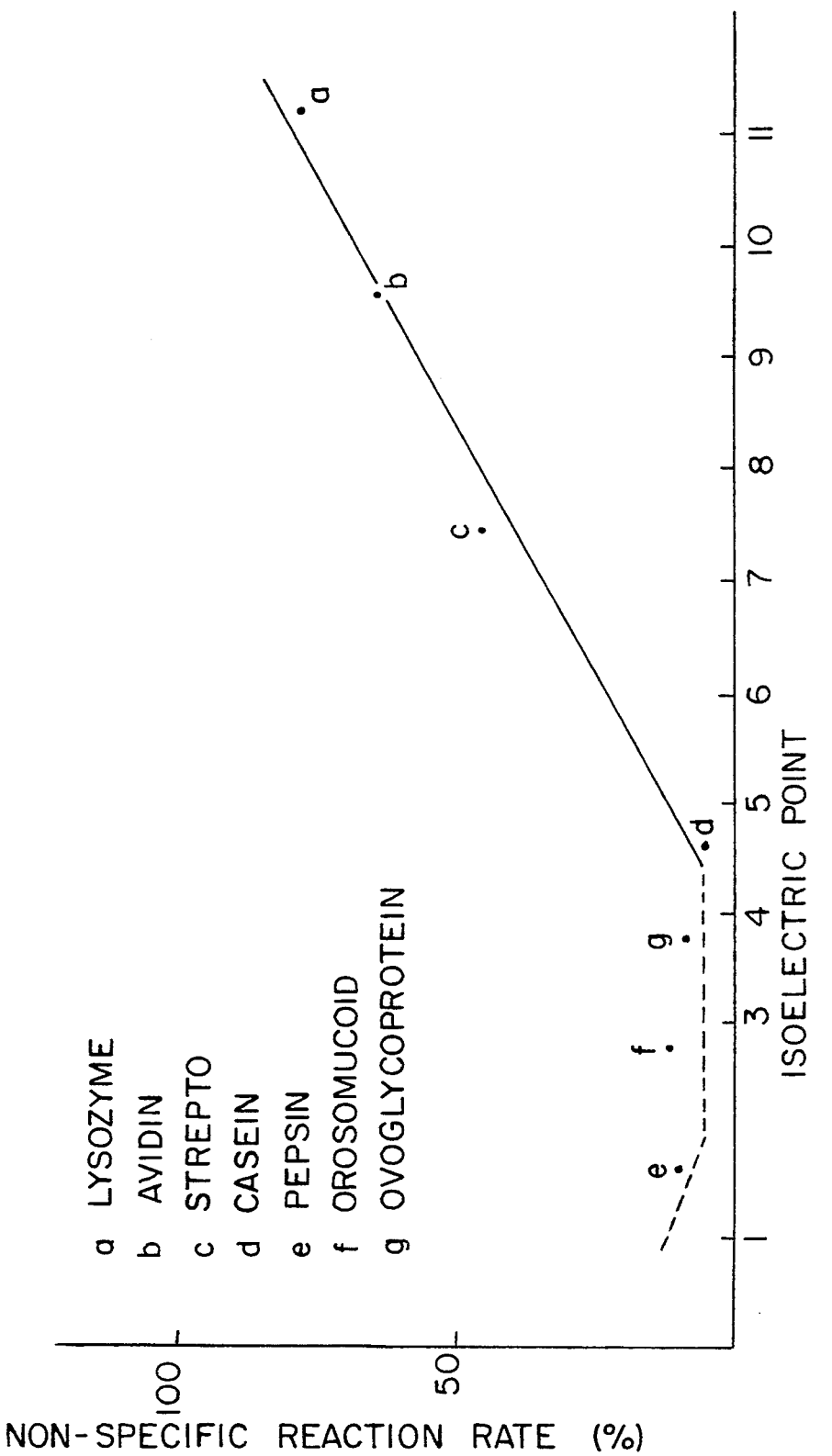
FIG. 11 shows the relationship between the nonspecific reaction rate and isoelectric points of various proteins.

Using the following calculation formula, the nonspecific reaction ratio was calculated, and the correlation with molecular weight or isoelectric point obtained as shown in FIG. 10 and FIG. 11, respectively.

$$\text{Nonspecific reaction ratio} = \frac{OD\ 650\ (0\ ng/ml)}{OD\ 650\ (100\ ng/ml)} \times 100$$

From FIG. 10 and FIG. 11, it is evident that addition of a protein having a molecular weight within the range of 16,000 to 50,000 causes a remarkable lowering of nonspecific reaction. Also, from FIG. 11, it is understood that addition of a protein with an isoelectric point of 1.0 to 5.0 gives a good reduction of nonspecific reaction.

Example 10

Influence on immunoreaction by addition of various concentrations of orosomucoid or pepsin Using polystyrene balls having the polyclonal antibody to human plasminogen fixed thereon and the anti-human $\alpha_2$ PI monoclonal antibody labelled with peroxidase, in 0.1M phosphate buffer (pH 7.2) containing orosomucoid or pepsin at various concentrations, incubation was performed at 37° C. for 60 minutes at respective levels of human $\alpha_2$ PI-plasmin conjugate concentration of 0, 50 and 100 ng/ml. The balls were separated from the reaction mixture and the balls thoroughly washed with physiological saline. Then, the balls were permitted to react in an aqueous solution containing the color forming system of tetramethylbenzidine $H_2O_2$ and the enzymatic reaction was stopped by addition of a reaction stopping agent, followed by measurement of the absorption strength at 650 nm wavelength.

Figure 12:
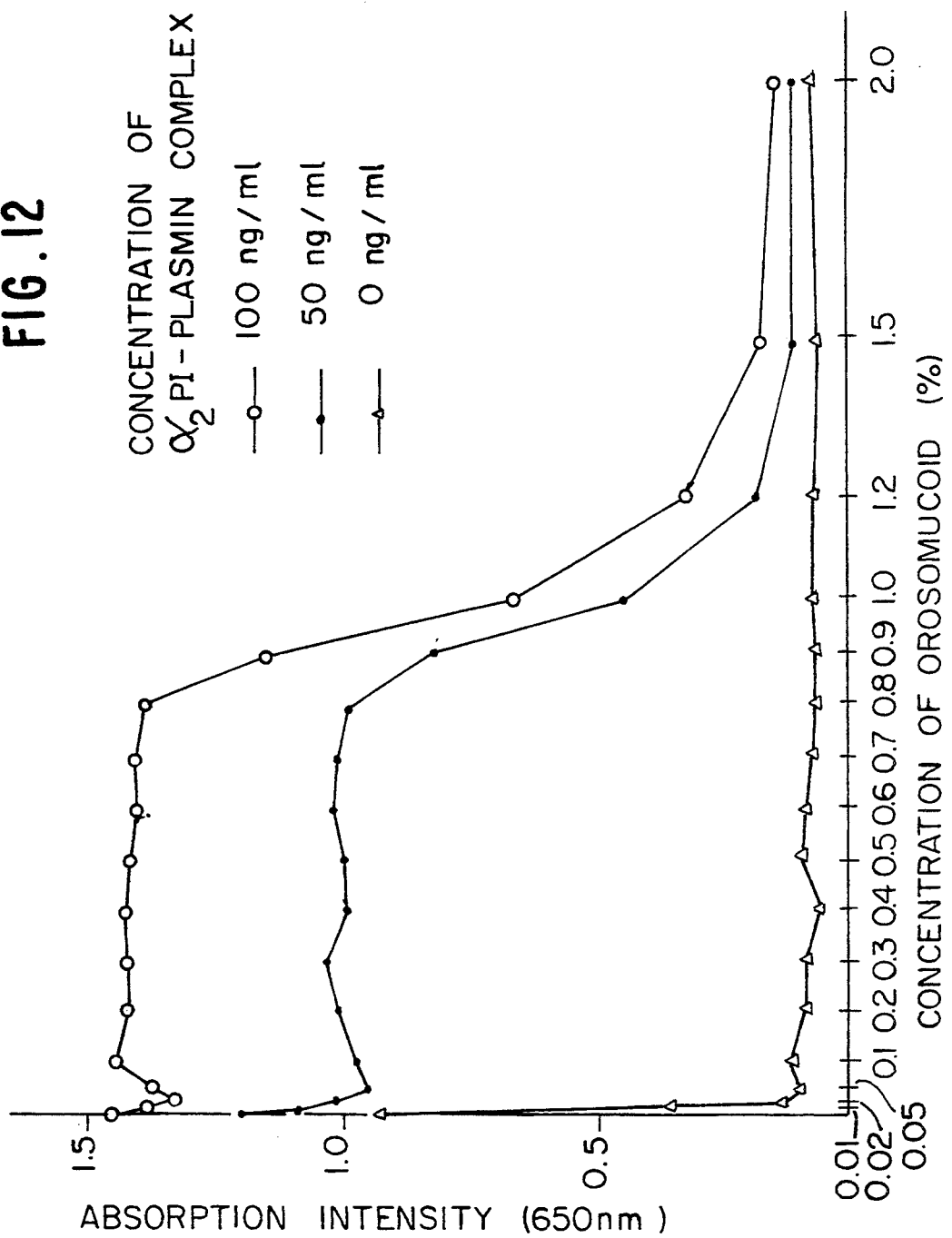
FIG. 12 shows the influence on the immunoreaction of the concentration of the added orosomucoid.
Figure 13:
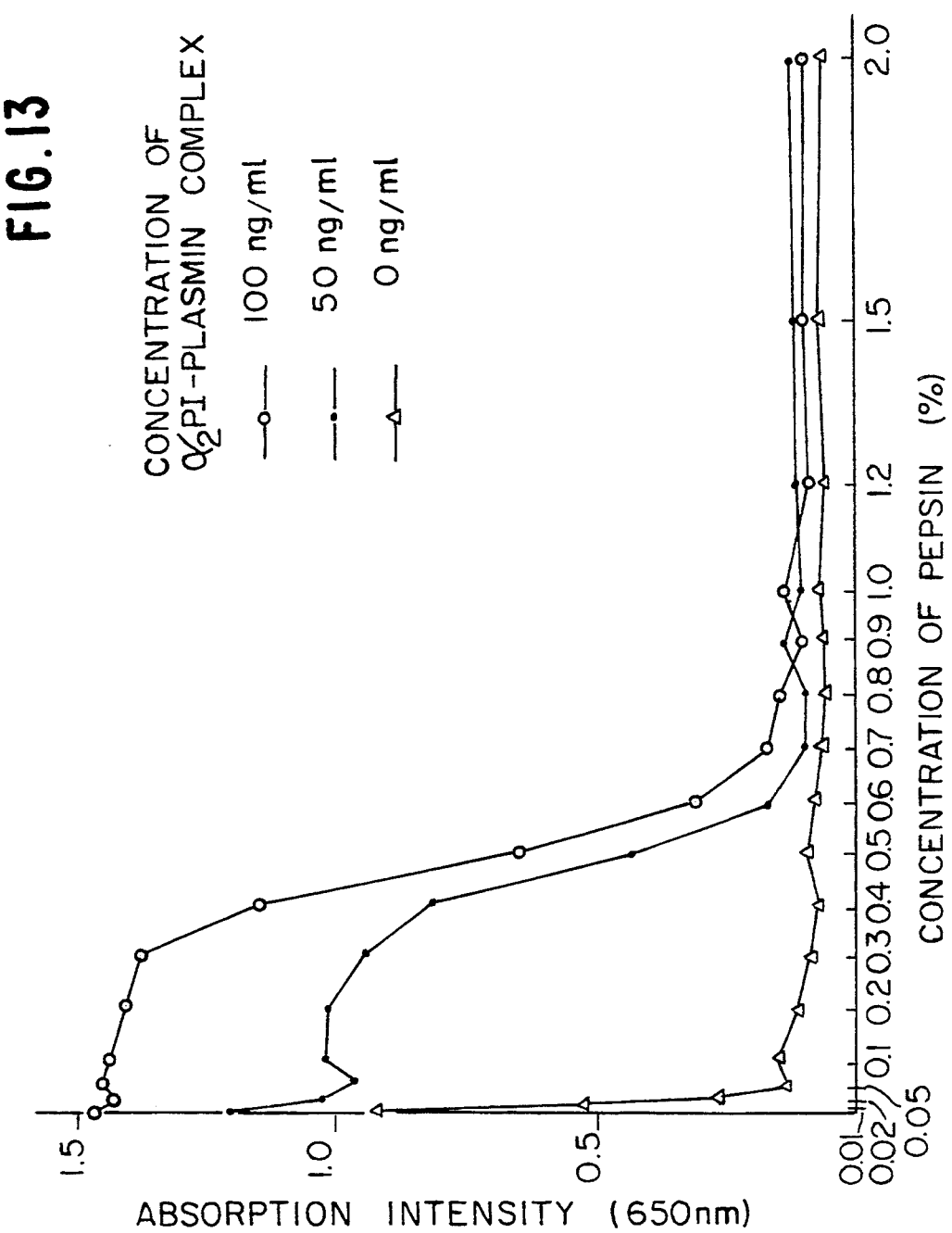
FIG. 13 shows the influence on the immunoreaction of the concentration of the added pepsin.

The results are shown in FIG. 12 (orosomucoid) and FIG. 13 (pepsin), respectively. From FIG. 12 and FIG. 13, it is clear that nonspecific reaction remarkably is increased at a low protein concentration and that the specific reaction is decreased at a high protein concentration.

Example 11

Skim milk addition test in lung-surfactant apoprotein measurement system

A 0.50 ng/ml solution of human lung surface apoprotein (hereinafter called LSP) was prepared in a buffer for immunoassay (1% bovine serum albumin, 0.01M phosphate, 0.85% NaCl buffer, pH 7.2) and 100 μl thereof, 100 μl of a skim milk containing solution controlled to the final concentration with the same buffer as mentioned above to 0, 0.1, 0.2, 0.3, 0.4, 0.5, 0.6 and 0.7%, and 200 μl of the same buffer as mentioned above containing the anti-human LSP monoclonal antibody labelled with horseradish peroxidase were placed in a test tube and well mixed. To the mixture, one bead having the anti-LSP monoclonal antibody fixed thereon was added to each test tube, and the incubation was carried out at 45° C. for 30 minutes. Then, after the solution was suction removed, the bead was washed with 2 ml of physiological saline 3 times, and to each 0.4 ml of 0.1M phosphate-citrate buffer (pH 4.0) containing 0.02% 3,3',5,5'-tetramethylbenzidine and 2.5 mM $H_2O_2$ were added to carry out incubation at 45° C. for 15 minutes, followed by addition of 1 ml of 1N aqueous sulfuric acid as the reaction stopping agent to stop the enzymatic reaction.

Figure 14:
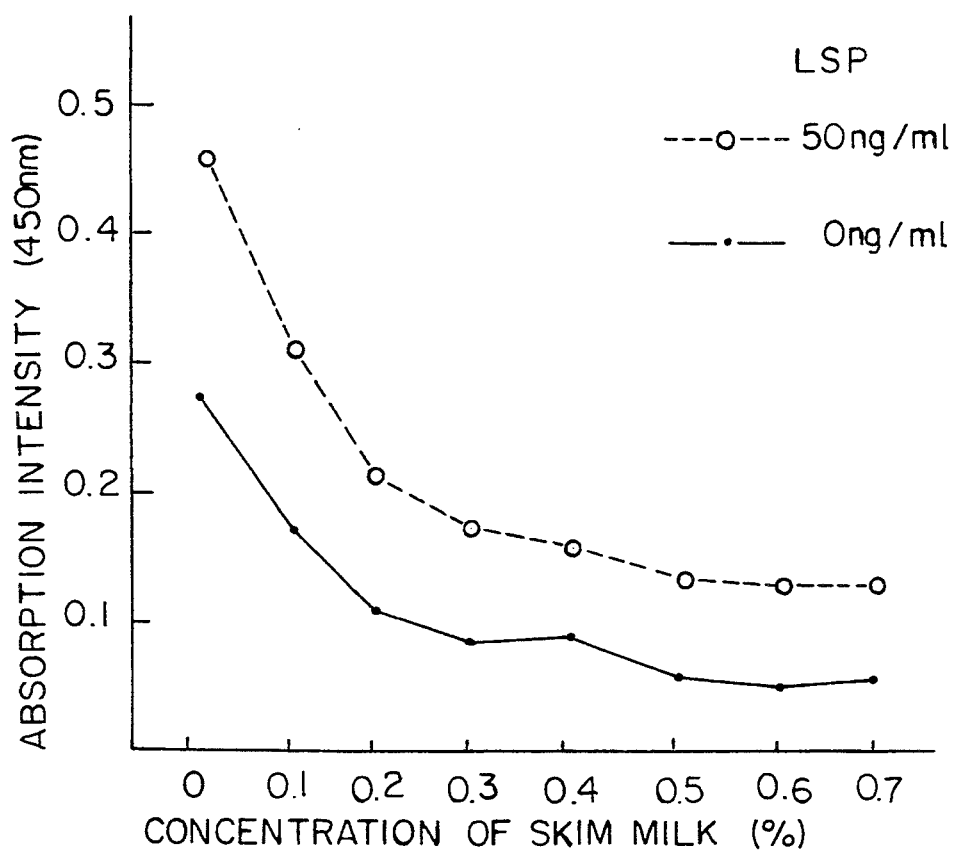
FIG. 14 shows the influence on the immunoreaction of the concentration of skim milk added to the measurement system of human lung surface apoprotein.

Then, the solutions were subjected to measurement of the absorption intensity (O.D.) at 450 nm with purified water as the control by using a spectrophotometer and the results are shown in FIG. 14.

We claim:

1. An immunoassay method to detect presence of an antigen selected from the group consisting of $\alpha 2$ plasmin inhibitor-plasmin conjugate, protein C, protein S, acidic glutathione S-transferase derived from human placenta, chrondrocalcin and IgA type immune complex in a sample suspected of containing said antigen comprising:

a. performing an antigen-antibody reaction in an aqueous solution by mixing an antibody which specifically binds said antigen in said sample in the presence of a non-specific reaction controller consisting of skim milk, wherein the final concentration of the non-specific reaction controller in the aqueous solution is 0.02 to 0.8% by weight, and b. detecting the amount of antigen-antibody complexes in said aqueous solution, wherein the amount of said complexes correlates with the amount of antigen in said sample.

2. An immunoassay method to detect presence of an antigen, wherein said antigen is $\alpha 2$ plasmin inhibitor, in a sample suspected of containing said antigen comprising:

a. performing an antigen-antibody reaction in an aqueous solution by mixing an antibody which specifically binds said antigen in said sample in the presence of a non-specific reaction controller selected from the group consisting of pepsin, skim milk, and orosomucoid, wherein the final concentration of the non-specific reaction controller in the aqueous solution is 0.02 to 0.8% by weight, and b. detecting the amount of antigen-antibody complexes in said aqueous solution, wherein the amount of said complexes correlates with the amount of antigen in said sample.

3. A method as claimed in claim 2 wherein said antigen-antibody reaction controller is skim milk.

4. A reagent kit for an immunoassay, said immunoassay occurring in an aqueous solution to detect the presence of an antigen selected from the group consisting of $\alpha 2$ plasmin inhibitor-plasmin conjugate, protein C, protein S, acidic glutathione S-transferase derived from human placenta, chrondrocalcin and IgA type immune complex comprising:

(a) an enzyme-labelled antibody which specifically binds said antigen, (b) antibody-fixed beads, wherein said antibody-fixed beads specifically binds said antigen, (c) an assay buffer comprising a non-specific reaction controller consisting of skim milk wherein said assay buffer said non-specific reaction controller is at a concentration of from 0.02 to 0.08% by weight, (d) a substrate solution, (e) a color forming agent, (f) a color forming stopping solution, (g) a standard, and (h) a washing solution.

5. A reagent kit for an immunoassay that occurs in an aqueous solution to detect the presence of $\alpha 2$ plasmin inhibitor wherein said kit comprises:

(a) an enzyme-labelled antibody which specifically binds said antigen, (b) antibody-fixed beads, wherein said antibody-fixed beads specifically binds said antigen, (c) an assay buffer comprising a non-specific reaction controller selected from the group consisting of pepsin, skim milk and orosomucoid wherein said assay buffer said non-specific reaction controller is at a concentration of from 0.02 to 0.08% by weight, (d) a substrate solution, (e) a color forming agent, (f) a color forming stopping solution, (g) a standard, and (h) a washing solution.

6. A reagent kit as claimed in claim 5 wherein said non-specific reaction controller is skim milk.

* * * * *